United States Patent [19]

Millington

[11] 4,428,924
[45] * Jan. 31, 1984

[54] PREPARATION FOR DIAGNOSTIC RADIOLOGY

[75] Inventor: Arthur R. Millington, Blackburn, England

[73] Assignee: Linton Medical Services Limited, Blackburn, England

[*] Notice: The portion of the term of this patent subsequent to Jul. 29, 1997 has been disclaimed.

[21] Appl. No.: 139,980

[22] Filed: Apr. 14, 1980

Related U.S. Application Data

[63] Continuation-in-part of Ser. No. 874,154, Feb. 1, 1978, Pat. No. 4,215,103.

[30] Foreign Application Priority Data

Feb. 2, 1977 [GB] United Kingdom ................. 4319/77

[51] Int. Cl.$^3$ .............................................. A61K 49/04
[52] U.S. Cl. .......................................................... 424/4
[58] Field of Search ............................................. 424/4

[56] References Cited

U.S. PATENT DOCUMENTS 2,659,690 11/1953 Slaybaugh ................................ 424/4
3,689,630 9/1972 Kikuchi et al. .......................... 424/4

Primary Examiner—Frederick E. Waddell
Attorney, Agent, or Firm—Fleit, Jacobson, Cohn & Price

[57] ABSTRACT

A method for making a preparation for diagnostic radiology. The method consists of agitating a radio opaque substance and a carrier in a vessel, controlling temperature and pressure, admitting gas to the vessel and withdrawing mixture from the vessel such that dissolved gas does not fall below a level at which gas is released within the patient when the preparation is ingested.

7 Claims, 4 Drawing Figures

PREPARATION FOR DIAGNOSTIC RADIOLOGY

This is a continuation-in-part of application Ser. No. 874,154 filed Feb. 1, 1978 now U.S. Pat. No. 4,215,103.

The invention relates to a preparation for diagnostic radiology and a method and apparatus for producing such preparation.

Recent investigations into the effectiveness of radiological examination of lesions in the upper gastro intestinal tract have revealed that the conventional barium meal taken by the patient prior to such examination does not enable small lesions, such as shallow ulcers, and flat or surface ulcers, to be detected. Additionally, it has been found that the conventional barium meal cannot reliably be counted on to enable any difference between benign and malignant ulcers to be noted.

In order to deal with this problem proposals have been made for expanding or distending the part under examination by introducing into the intestine powder, granules or tablets which release carbon dioxide. An alternative proposal comprises introducing air to the desired location in the intestine by means of a tube. However, neither of these techniques is entirely satisfactory.

A further problem associated with barium sulphate is that it relatively quickly settles out of suspension and that can, unless steps are taken, create an uneven coating on the part of the patient under examination. In order to maintain the barium sulphate in suspension it has been proposed to carbonate the suspension. This has the effect of agitating the suspension when it is administered to a patient. The carbonation of the suspension was not intended to, nor did it, provide for any expansion or distension of organs within the patient.

If the preparation is to provide an adequate contrast medium within the patient it is, of course, important that the radio opaque constituent should adequately coat the surfaces to be examined. In other words it is important that there should be a sufficient amount of barium sulphate or other radio opaque substance in the preparation ingested by the patient to coat the surfaces to be examined. Because of that requirement it has become the practice to use preparations of increasingly high barium sulphate concentration but that yet further increases the difficulty of maintaining the suspension uniform and with sufficiently low viscosity.

The present invention has been made in an attempt to deal with the above problems and has for its object the provision of a method and apparatus for making a preparation for diagnostic radiology in which the radio opaque medium is substantially uniformly distributed therein at high concentrations and which remain substantially uniformly distributed during ingestion, which expands or distends the part of the patient to be examined, which forms a substantially uniform coating on the part under examination.

Accordingly the invention provides a method of producing a preparation as defined above comprising agitating in a pressure vessel a suspension of a radio opaque substance in a carrier, admitting gas to the vessel during said agitation, controlling the temperature and pressure within the vessel, and withdrawing the preparation from the vesel for administration to a patient in such a way as to ensure that the concentration of dissolved gas does not fall below a level at which gas is released within the patient when the preparation is ingested.

The gas employed in the invention is preferably carbon dioxide. However, any other gas or mixture of gases can be used provided it is not harmful to the patient, for example a mixture of equal volumes of carbon dioxide and nitrogen.

The concentration of gas can be varied within the above limitation that there must be sufficient present to be released when the preparation is ingested. Generally from three to four parts of gas per part of preparation by volume is found to give good results.

The constituents of the preparation, into which the gas is incorporated are known per se and are selected in accordance with the mixture of the particular diagnosis to be performed. Generally, however, the radio opaque substance is barium sulphate and the carrier is water. If desired, additives such as anti-foaming agents can be included in the preparation in order to prevent or reduce the effect of any foam, formed when gas is released on radiological examination.

Preferably the step of dissolving the gas in the preparation is carried out at reduced temperature and/or elevated pressure. It is also preferred that the surface area of preparation brought into contact with the gas be as large as possible.

Agitation of the mixture is preferably carried out by mechanical means such as a rotatable disc or paddle within the vessel. Alternatively the vessel can be movably mounted so that it can be rocked to create turbulence of the mixture therewithin. Agitation may also be obtained by ultrasonic bombardment, or by a variable electromagnetic field being applied to agitate inert magnetic particles added to the mixture. A transducer may also be employed for agitation if desired.

The invention also provides apparatus for producing a preparation for diagnostic radiology, comprising a pressure vessel, means for admitting a carrier and a radio opaque substance to the vessel, means for admitting a gas to the vessel, means for agitating the contents of the vessel in order to produce a substantially uniform suspension of radio opaque substance in the carrier and to assist the gas to dissolve in the preparation, means for controlling the temperature and pressure in the vessel and means for withdrawing preparation from the vessel for administration to a patient in such a way as to ensure that the concentration of dissolved gas does not fall below a level at which gas is released within the patient when the preparation is ingested.

In this specification reference is made to the gas being dissolved in the preparation. This term is intended to include both gas which is dissolved in the preparation which will account for all or the bulk of the incorporated gas and also gas which may be included in some other way for example by adsorption onto the surface of the solids in the preparation.

The preparation can be made in a concentrated form and diluted prior to administration to the patient.

Specific embodiments of the invention will now be described by way of example with reference to the accompanying drawings in which.

Figure 1:
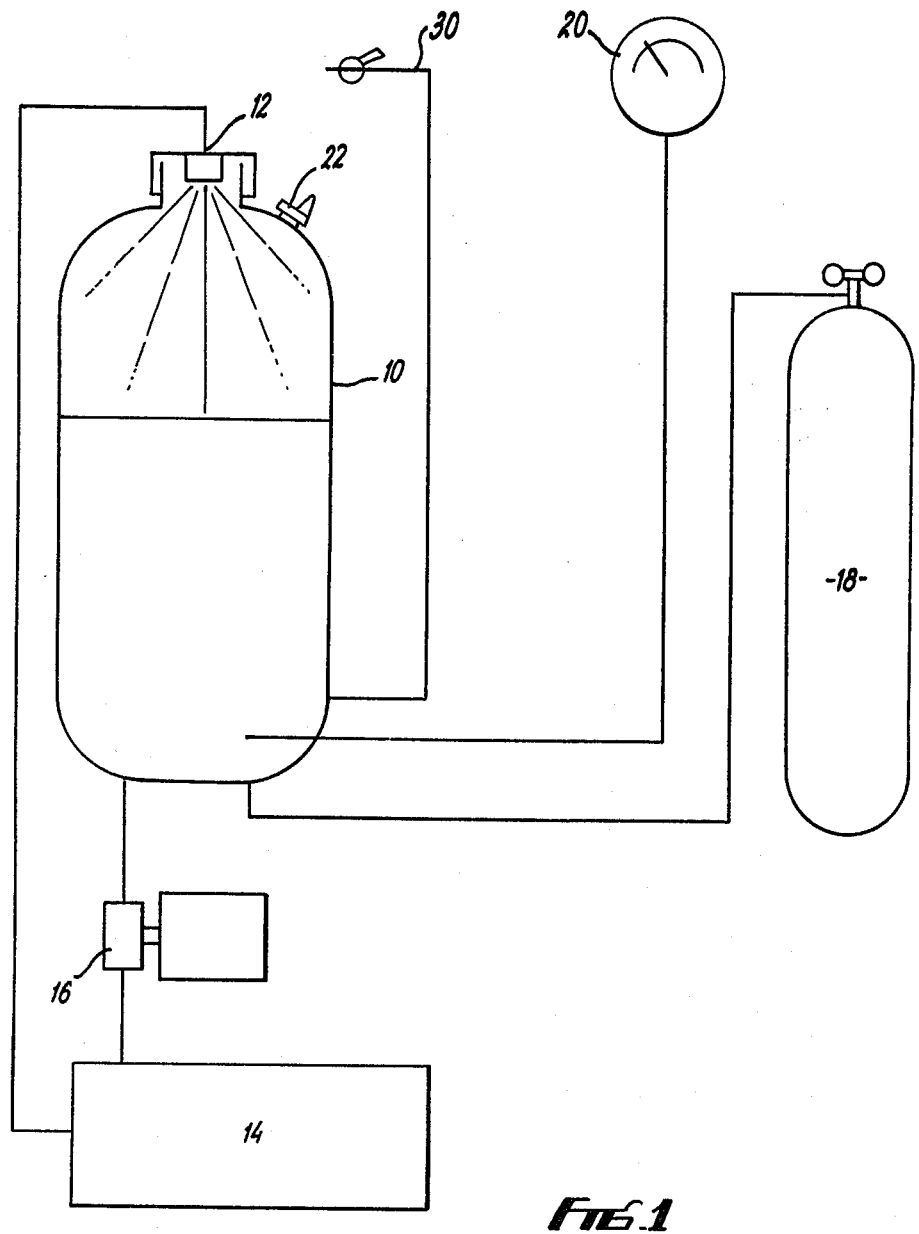
FIG. 1 shows diagrammatically one form of apparatus for making a preparation according to the invention.

Referring to FIG. 1 of the drawings, a pressure vessel 10 is provided with an inlet 12 in the form of a spray at the top thereof. The inlet 12 is connected to the bottom of the vessel through cooling means 14 and a pump 16. A container 18 of carbon dioxide gas under pressure is also connected to the bottom of the vessel 10.

The vessel is also fitted with a temperature measuring means 20 and pressure regulator 22.

In order to make a preparation according to the invention the vessel 10 is partially filled with a preparation known per se for example a barium preparation. Carbon dioxide gas is admitted to the vessel 10 from the container 18, air in the vessel being vented through regulator 22. When the vessel contains the predetermined quantities of barium preparation and gas the pump is switched on and the contents of the vessel cycled through the cooling means 14 and the spray 12 until the desired level of dissolved gas is attained. The resulting preparation can then be drawn for use from the vessel through line 30.

Most radio opaque substances, including barium sulphate tend to settle out from diagnostic radiology preparations. In order to combat that it is desirable that the preparation be thoroughly mixed at least prior to use. Such mixing is achieved in the apparatus just described by the agitation imparted during cycling of the preparation through the cooling means and spray. However, agitation to produce uniform or substantially uniform distribution of the radio opaque substance in the preparation may be produced by other means.

Figure 2:
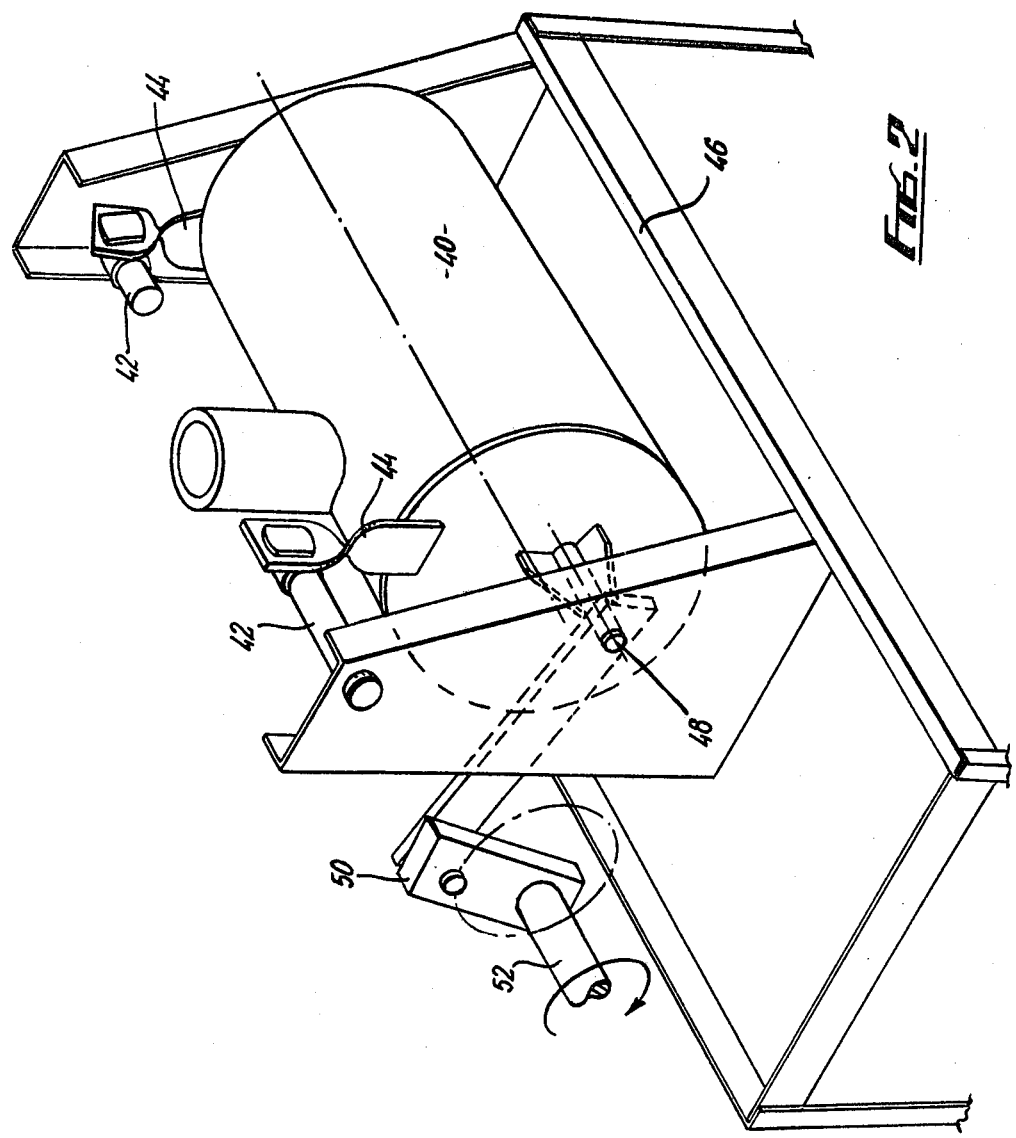
FIG. 2 is a perspective view of another embodiment of apparatus for making a preparation according to the invention.

For example, as illustrated in FIG. 2, a cylindrical vessel 40, for mixing the preparation is slung on shafts 42, by means of straps 44 fixed one at each end of the vessel and journalled on the said shafts. The shafts are supported on a frame 46.

A stub axle 48 projects from an end face of the vessel 40 parallel to but displaced from the axis of the vessel, one arm of a crank 50 being pivotally mounted on the stub axle. The other arm of the crank is connected by shaft 52 to a drive motor (not shown). When the motor is energised the vessel is rocked back and forth thereby agitating the contents.

Figure 3:
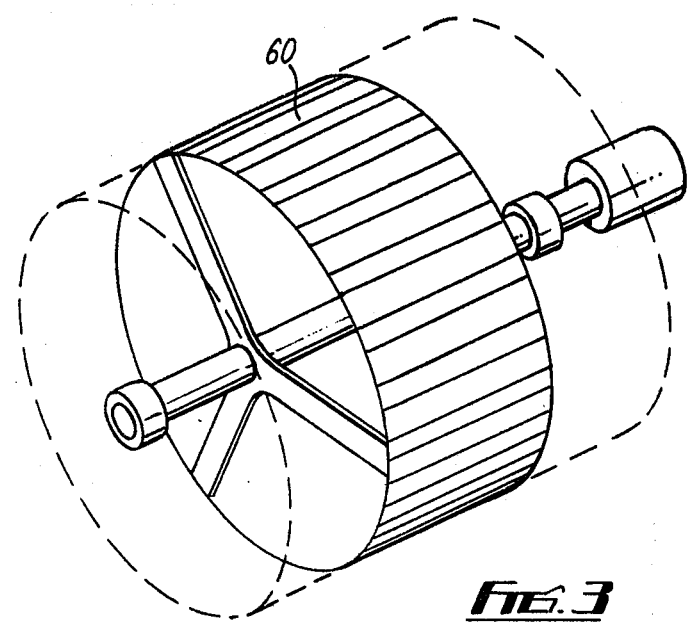
FIGS. 3 and 4 illustrate two further means for agitation of the preparation.
Figure 4:
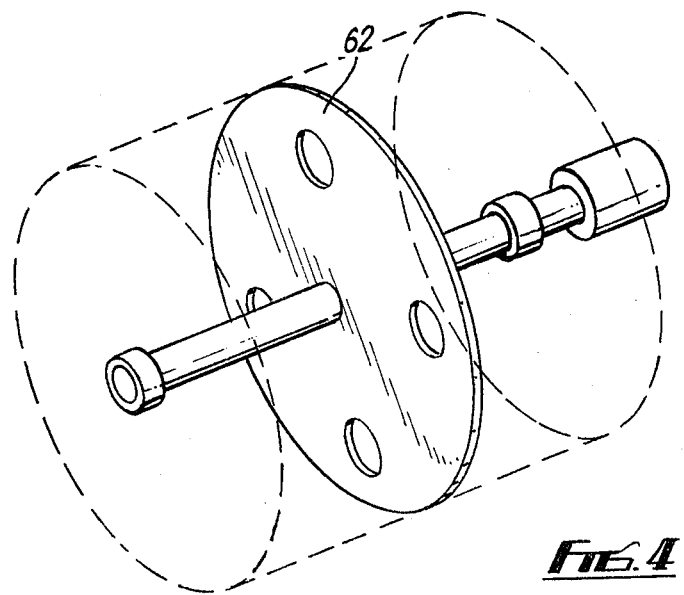

Other useful apparatus for agitation of the preparation comprise a paddle wheel 60 rotatably mounted in the vessel (FIG. 3) and an aperture disc 62 rotatably mounted in the vessel (FIG. 4).

The apparatus of the invention enables large batches of preparation to be made up, and hence more accurate proportioning of the constituents to be obtained. Since the vessel from which doses are withdrawn can be agitated to maintain a uniform suspension it is possible to omit from the preparation some or all of the suspension agents which prior art preparations normally contain.

Because of the even coating of radio opaque medium within the patient, due to release of dissolved gas after ingestion, it is not necessary for the patient to take a large dose of the preparation. Thus even though the preparation has a high concentration of radio opaque medium, in small doses it does not become too unpalatable and does not adversely affect the digestive system of the patient.

The concentration of dissolved gas, as stated depends on both pressure and temperature. For example, using the above described apparatus and holding the pressure constant at 40 p.s.i.g. the amount of dissolved gas varies with temperature as illustrated by the following figures.

| Temperature °F. | Parts by volume dissolved gas/part by volume of water |
|---|---|
| 40 | 5.1 |
| 45 | 4.7 |
| 50 | 4.3 |
| 55 | 3.9 |
| 60 | 3.6 |
| 65 | 3.3 |
| 70 | 3.1 |
| 75 | 2.9 |
| 80 | 2.6 |
| 85 | 2.45 |
| 90 | 2.3 |
| 95 | 2.15 |
| 100 | 2 |

The following Examples further illustrate the invention.

EXAMPLE 1

A proprietory barium sulphate preparation sold under the Trade Mark "Micropaque" and which contains from 56.8 to 57.8% wt/wt of barium sulphate was gasified with carbon dioxide using the apparatus of the kind described above. A quantity of Micropaque containing 100 g solids was placed in the apparatus, the pressure adjusted to 20 p.s.i.g and the temperature held at 5° C. The gas uptake was found to be 524 ml. The process was repeated a further five times and the gas uptake found to be 540 ml, 534 ml, 538 ml, 578 ml, 590 ml the average gas uptake being 551 ml against a theoretical gas uptake of 265 ml.

EXAMPLE 2

The same procedure was followed as in Example 1 except that the temperature was raised to 15° C. The gas uptake in five repeated processes was found to be 386 ml, 576 ml, 517 ml, 517 ml and 540 ml giving an average gas uptake of 507 ml against a theoretical gas uptake of 200 ml.

EXAMPLE 3

The same procedure was followed as in Example 2 except that the gas was changed to a gas mixture of equal volumes of $CO_2$ and $N_2$. Gas uptake found in four repeated processes was 246 ml, 243 ml, 228 ml, and 231 ml giving an average gas uptake of 237 ml against a theoretical gas uptake of 100 ml.

EXAMPLE 4

The procedure employed in Example 1 was followed but with the pressure raised to 40 p.s.i.g. The process was repeated six times to give gas uptake figures of 692 ml, 694 ml, 711 ml, 543 ml, 654 ml, and 561 ml, the average gas uptake being 642 ml against a theoretical gas uptake of 420 ml.

EXAMPLE 5

The procedure of Example 4 was followed using a different batch of "Micropaque." Four repeats of the process gave gas uptake figures of 460 ml, 461 ml, 470 ml and 464 ml, the average gas uptake being 464 ml.

EXAMPLE 6

The same procedure was followed as in Example 2 but with the pressure raised to 40 p.s.i.g. The process was carried out twice and the gas uptake on both occasions was found to be 689 ml against a theoretical gas uptake of 315 ml.

EXAMPLE 7

The procedure of Example 6 was followed using a different batch of "Micropaque" (the same batch as employed in Example 5). Gas uptake figures obtained were 402 ml, 404 ml, 409 ml, 418 ml, 417 ml and 413 ml the average being 410 ml.

EXAMPLE 8

A proprietory dry barium sulphate preparation sold under the Trade Mark "E-Z" Paque" was mixed with water to form a 53% w/w dispersion. A quantity of the dispersion containing 100 g solids was gasified with $CO_2$ at 5° C. at 20 p.s.i.g. The process was repeated twelve times and the gas uptake found to be as follows: 375 ml, 376 ml, 385 ml, 379 ml, 417 ml, 411 ml, 386 ml, 363 ml, 330 ml, and 367 ml respectively, the average being 379 ml against a theoretical gas uptake of 323 ml.

EXAMPLE 9

The same procedure was followed as in Example 8 except that the temperature was 15° C. The process was repeated eight times to give gas uptake figures in ml of 264, 265, 254, 266, 279, 280, 280 and 279, the average being 271 ml against a theoretical gas uptake of 232 ml.

EXAMPLE 10

The same procedure was followed as in Example 8 except that the pressure was 40 p.s.i.g. The process was repeated six times to give gas uptake figures in ml of 495, 494, 525, 540, 506, and 508, the average being 511 ml against a theoretical gas uptake of 510 ml.

EXAMPLE 11

The same procedure was followed as in Example 10 except that the dispersion was made up as 56% w/w. The process was repeated six times to give gas uptake figures, in ml, of 423, 448, 480, 486, 454, and 457, the average being 458 ml against a theoretical gas uptake of 451 ml.

EXAMPLE 12

The same procedure was followed as in Example 10 except that the dispersion was made up as 72% w/w. The process was repeated six times to give gas uptake figures, in ml, of 346, 259, 252, 272, 248 and 280, the average being 276 ml against a theoretical gas uptake of 224 ml.

EXAMPLE 13

The same procedure was followed as in Example 9 except that the pressure was 40 p.s.i.g. The process was repeated eight times to give gas uptake figures, in ml, of 338, 445, 343, 332, 371, 409, 421 and 346, the average being 375 ml against a theoretical gas uptake of 366 ml.

EXAMPLE 14

A proprietory dry barium sulphate preparation marketed as "Baritop G" was mixed with water to form a 64.0% w/w dispersion. A quantity of the dispersion containing 100 g solids was gasified with $CO_2$ at a temperature of 5° C. and pressure of 20 p.s.i.g. The process was repeated six times to give gas uptake figures, in ml, of 254, 253, 248, 247, 251 and 255, the average being 251 ml against a theoretical gas uptake of 205 ml.

EXAMPLE 15

The procedure of Example 14 was followed but with the temperature at 15° C. The process was repeated six times giving gas uptake, in ml, of 185, 187, 182, 182, 193 and 193, the average being 187 ml against a theoretical gas uptake of 147 ml.

EXAMPLE 16

The same procedure was followed as in Example 14 except that the gas was a mixture of equal volumes of $CO_2$ and $N_2$. The process was repeated six times, the gas uptake figures being, in ml, 137, 138, 144, 143, 140 and 141, average 140 ml against a theoretical gas uptake of 102 ml.

EXAMPLE 17

The procedure of Example 14 was followed but with the pressure adjusted to 40 p.s.i.g. The process was repeated six times, the gas uptake figures, in ml, being 340, 346, 319, 322, 330 and 344, the average being 334 ml against a theoretical gas uptake of 323 ml.

EXAMPLE 18

The procedure of Example 15 was followed but with the pressure adjusted to 40 p.s.i.g. The process was repeated four times and the gas uptake figures, in ml, were 270, 269, 288 and 289, the average being 270 ml against a theoretical gas uptake of 232 ml.

EXAMPLE 19

The same procedure was followed as in Example 16 but with the pressure adjusted to 40 p.s.i.g. The process was repeated six times and the gas uptake figures were, in ml, 194, 195, 203, 199, 202 and 196 the average being 198 ml against a theoretical gas uptake of 161 ml.

What is claimed is:

1. A method of producing a preparation for diagnostic radiology, the preparation, when taken into the body of a user, releasing a gas that expands within the body of a user, comprising:
   placing a mixture containing a radio opaque substance and a carrier in a pressure vessel, the radio opaque substance being present in a quantity sufficient for diagnostic radiology;
   adding a non-toxic gas to the pressure vessel;
   agitating the mixture for a period of time sufficient to produce a substantially uniform suspension of radio opaque substance in the carrier and to obtain a predetermined level of dissolved gas within the mixture, the level being sufficient to cause release of the gas within the body of a user;
   controlling the temperature and pressure within the vessel so that the temperature is below ambient and the pressure is elevated; and
   withdrawing the preparation from the vessel for administration to a patient in such a way that the concentration of dissolved gas does not fall below a level at which gas is released within the patient when the preparation is ingested.

2. A method as claimed in claim 1, wherein the gas is carbon dioxide.

3. A method as claimed in claim 1, wherein the gas is nitrogen.

4. A method as claimed in claim 1, wherein the gas is a mixture of carbon dioxide and nitrogen.

5. A method as claimed in claim 1, wherein the radio opaque substance is barium sulphate.

6. A method as claimed in claim 1, wherein the preparation is continuously agitated.

7. A method as claimed in claim 1, wherein the agitation is mechanical.

* * * * *